United States Patent [19]

Stockel

[11] Patent Number: 5,312,586
[45] Date of Patent: May 17, 1994

[54] PROCESS FOR STERILIZING A CONTACT LENS

[76] Inventor: Richard F. Stockel, 475 Rolling Hills Rd., Bridgewater, N.J. 08807

[21] Appl. No.: 991,335

[22] Filed: Dec. 16, 1992

Related U.S. Application Data

[63] Continuation-in-part of Ser. No. 719,169, Jun. 21, 1991, abandoned.

[51] Int. Cl.$^5$ .......................... A61L 2/18; C02F 1/42; B01J 39/24
[52] U.S. Cl. ...................................... 422/37; 514/840; 210/668
[58] Field of Search ................... 422/37, 28, 292, 159; 514/839, 840; 424/78.04; 210/668

[56] References Cited

U.S. PATENT DOCUMENTS

| | | | |
|---|---|---|---|
| 3,912,451 | 10/1975 | Gaglla | 422/30 |
| 4,167,561 | 9/1979 | Lamberti | 424/665 |
| 4,444,785 | 4/1984 | Mandt | 514/840 |
| 4,472,281 | 9/1984 | Kerridge | 210/668 |
| 4,495,152 | 1/1985 | Yan et al. | 422/159 |
| 4,880,601 | 11/1989 | Andermann et al. | 422/28 |
| 4,889,689 | 12/1989 | Tsao | 422/28 X |
| 4,976,921 | 12/1990 | Itagaki | 422/28 |
| 4,978,483 | 12/1990 | Redding | 264/4.32 |
| 5,011,661 | 4/1991 | Schäfer et al. | 422/28 X |

OTHER PUBLICATIONS

"Peroxygen Disinfectants" by M. G. C. Baldry and K. Dickinson, *Specialty Chemicals*, 1983, pp. 17 et seq.

*Primary Examiner*—Robert J. Warden
*Assistant Examiner*—E. Leigh Dawson
*Attorney, Agent, or Firm*—Jack Matalon

[57] ABSTRACT

Process for sterilizing a contact lens using an aqueous solution of a sterilant which may be a peroxygen disinfectant, an inorganic hypochlorite compound or a hypochlorite precursor compound. The process involves the steps of contacting the lens with the aqueous solution for a period of time sufficient to effect sterilization of the lens; and thereafter contacting the resultant aqueous solution and lens with an amount of activated carbon and for a period of time sufficient to decompose substantially all of any residual sterilant to ophthalmologically innocuous by-products.

10 Claims, No Drawings

PROCESS FOR STERILIZING A CONTACT LENS

REFERENCE TO RELATED APPLICATION

This application is a continuation-in-part of Ser. No. 07/719,169 filed Jun. 21, 1991, abandoned.

FIELD OF THE INVENTION

The present invention relates to a process for sterilizing a contact lens. More particularly, the invention relates to a process for converting substantially all of any sterilant which remains after sterilization of the contact lens into ophthalmologically innocuous by-products using activated carbon.

BACKGROUND OF THE INVENTION

Processes for sterilization of contact lenses are well known in the prior art. Typically such processes employ aqueous solutions of sterilants such as $H_2O_2$ present in a concentration of 1–5 wt. %, together with adjuvants such as chelating agents (e.g. ethylenediaminetetraacetic acid), buffering agents such as alkali metal phosphates, alkali metal borates, alkali metal carbonates and mixtures thereof, etc.

After a contact time sufficient to disinfect the lens, the residual sterilant must be neutralized, i.e. converted into ophthalmologically innocuous by-products, since even traces of the sterilant remaining on the lens will result in irritation to the eye and concomitant discomfort to the contact lens wearer.

The most common method for neutralizing $H_2O_2$ involves the use of a thin film of platinum on a plastic substrate, as disclosed in U.S. Pat. No. 3,912,451. Such prior art process suffers from several disadvantages. Firstly, this process is quite expensive, owing to the use of platinum. Of course, the device may be reused a number of times (up to a maximum of ~100 times), but frequently the user continues to use the device well after the recommended maximum number of times, either because of inadvertence or to try to achieve further cost savings. Moreover, the decomposition rate of the $H_2O_2$ is non-reproducible and will gradually diminish, thus affording a lack of certainty as to the continued effectiveness of the device. Finally, there is also the need to dispose of an environmentally unfriendly material, i.e. platinum coated on a plastic substrate, since the device is not readily recyclable.

The prior art also teaches that chemical reducing agents, e.g. sodium thiosulfate, may be used to neutralize the residual $H_2O_2$, see A. R. Gasset et al., *Arch. Ophthalmol.*, vol. 93, June, 1975, pp. 412–415. It is also known to utilize a controlled-release sterilant system utilizing sodium percarbonate, see U.S. Pat. No. 4,863,627. However, such techniques are disadvantageous in that they introduce foreign substances which cause a change in the osmotic pressure of the ophthalmological solution and also a severe burning sensation in the eye or even irritation to the ocular tissue may result.

It is also known to use aqueous solutions of inorganic hypochlorites, i.e. alkali and alkaline metal hypochlorites as the sterilants for contact lenses together with reducing agents to neutralize the residual hypochlorite, see U.S. Pat. Nos. 3,717,580 and 4,167,561, Canadian Patent 1,087,955 and U.K. Patent 2,094,922.

U.S. Pat. No. 4,976,921 extends the concept of hypochlorite sterilants to compounds which are hypochlorite precursors, e.g. Chloramine-B, Chloraraine-T, Dichloramine-T, Halazone, chlorinated cyanuric acid, etc. It is taught that various reducing agents may be used to neutralize the residual hypochlorite precursors, e.g. sodium thiosulfate, $\alpha$- and $\beta$-hydroxy-carboxylic acids such as glycolic, malic, citric, lactic, tartaric, ascorbic, etc.

In many of the systems which employ slow-release inorganic hypochlorite or hypochlorite precursor compounds, a continuous loss of hypochlorite occurs which then entails higher concentrations of hypochlorite than otherwise needed. Such a situation may readily result in misuse by the consumer. Moreover, animal studies have shown that the use of hydroxy-carboxylic acids in the reduction of hypochlorites indicate that the reaction between these reactants produce physiologically irritating and perhaps toxic oxidation by-products, thereby limiting the usefulness of this method. In addition, all presently known methods of reducing hypochlorites bring about a concurrent change in the tonicity of the resulting aqueous solution, thereby causing discomfort to the contact lens wearer.

SUMMARY OF THE INVENTION

The present invention involves a process for sterilizing a contact lens with an aqueous solution containing a sterilant present in an amount sufficient to sterilize the lens. The sterilant is selected from the group consisting of peroxygen disinfectants, inorganic hypochlorite compounds and hypochlorite precursor compounds. The steps involved in the process comprise:

(a) contacting the lens with the aqueous solution for a period of time sufficient to effect sterilization of the lens; and thereafter (b) contacting the aqueous solution and lens resulting from step (a) with an amount of activated carbon and for a period of time sufficient to decompose substantially all of any residual sterilant to ophthalmologically innocuous by-products.

As mentioned above, the activated carbon causes the sterilant to decompose into ophthalmologically innocuous by-products. For example, in the case of hydrogen peroxide, the by-products are water and oxygen (which evolves from the aqueous solution) while in the case of sodium hypochlorite, the by-products are sodium chloride and oxygen (which evolves from the aqueous solution). Thus the present invention results in no irritating chemicals nor in any significant increase in tonicity which would otherwise cause discomfort to the contact lens wearer due to a buildup in osmotic pressure of the ocular fluid.

A further advantage of the present invention is its environmental friendliness. Some sterilant neutralization processes utilize devices which present a serious disposal problem, e.g. platinum-coated plastic. In other systems involving chemical reducing agents, the disposal of the reducing agent and attendant by-products may also present a disposal problem.

None of the disadvantages alluded to above are present in respect to the process of the present invention. Activated carbon is totally innocuous from a health and environmental point of view. Moreover, it is readily commercially available in many grades, particle sizes and forms and is very inexpensive, thus affording considerable economic savings versus other systems such as platinum coated on a plastic substrate. Such cost savings justify the use of the activated carbon on a one-time basis, thereby insuring consistent reproducibility of the sterilant neutralization reaction and avoiding the uncertainties attendant to the repetitive use of the same reduction system. However, if desired, as many as 50 neutralizations can be effected with the same charge of activated carbon without any significant loss of neutralization activity.

For the purposes of the present invention, it is preferred that the activated carbon have a surface area in excess of about 500 m$^2$/g. It is particularly preferred that the activated carbon have a pore volume of at least about 0.75 ml/g. The activated carbon may be used in many forms, e.g. powder, granules, sheets, rods, fiber, fabric, beads, extrudates, impregnated or coated on substrates, etc. Preferably, the activated carbon is not used in the form of fines which would come into direct contact with the aqueous solution containing the sterilant to be neutralized (i.e. decomposed or reduced). This may be readily and conveniently accomplished by providing the activated carbon in a container which is sealed except for a membrane which is permeable to the aqueous solution but is impermeable to the activated carbon. Alternatively, the activated carbon may be encapsulated in a water-swellable polymer which is permeable to the aqueous solution (but from which the activated carbon would not otherwise leach out). Non-limiting examples of useful water-swellable polymers include those prepared from ethyl cellulose, poly 2-hydroxymethyl methacrylate, ethylene-vinyl acetate copolymer, polyacrylic acid, etc. which may be utilized to form microcapsules completely enclosing the activated carbon. The apparatus and method for manufacturing such microcapsules is well known in the prior, e.g. see U.S. Pat. No. 4,978,483.

Typically, the amount of aqueous solution employed in step (a) is about 5 to 25 ml, preferably 10-20 ml, and the amount of activated carbon employed in step (b) is about 1 to 5 grams, preferably 1.5-3 grams (such amounts are employed in respect to a single contact lens).

In the sterilization step, i.e. step (a), the sterilant is present in the form of an aqueous solution. Where the sterilant comprises a peroxygen disinfectant, it may be a compound such as hydrogen peroxide (which is preferred), sodium carbonate peroxyhydrate, urea hydrogen peroxide, sodium perborate tetrahydrate, sodium perborate monohydrate, zinc peroxide, salts of Caro's acid such as potassium permonosulphate triple salt, peracetic acid, magnesium monoperoxyphthalate, etc. Such peroxygen disinfectants are well known in the prior art, e.g. see the article entitled "Peroxygen Disinfectants" by M. G. C. Baldry and K. Dickinson in *Specialty Chemicals*, November, 1983, p. 17 et seq. The peroxygen disinfectant is typically present in a concentration in the range of about 1 to 5 wt. %, preferably 2 to 4 wt. %, based on the weight of the aqueous solution.

Where the sterilant comprises an inorganic hypochlorite or hypochlorite precursor compound, the concentration may be considerably less, e.g. about 0.0005 to 0.5 wt. %, preferably 0.01 to 0.3 wt. %, based on the weight of the aqueous solution. Examples of suitable inorganic hypochlorite compounds include sodium hypochlorite (preferred), potassium hypochlorite, calcium hypochlorite, lithium hypochlorite, etc. Examples of suitable hypochlorite precursor compounds include Chloramine-B, Chloramine-T, Dichloramine-T, Halazone, chlorinated cyanuric acid, etc.

Regardless of which sterilant is employed, it is preferred that pH of the aqueous solution containing such sterilant be in the range of about 5 to 9, particularly 5.5 to 8.0. Typically, the aqueous solution containing the sterilant will be utilized at room temperature and will remain in contact with the lens for about 5 to 30 minutes before commencing step (b). In step (b), the activated carbon is typically permitted to remain in contact with the aqueous solution and lens resulting from step (a) at room temperature for about 1 to 6 hours. The temperatures are not critical, but room temperature is most practicable for the contact lens wearer.

The aqueous solution containing the sterilant which is employed in step (a) may also contain the usual adjuvants, e.g. chelating agents such as ethylenediaminetetraacetic acid which may be present in a concentration in the range of less than about 1 wt. %, based on the weight of the aqueous solution, in order to complex an trace metals present in the solution.

The aqueous solution containing the sterilant may also contain other components taught in the prior art for use in disinfecting contact lenses. For example, the solution may contain either an acid or base to adjust the pH and/or it may contain a tonicity adjusting agent. Acids are usually employed to neutralize alkaline hypochlorites while bases are employed to neutralize peroxygen disinfectants in order to achieve a desirable pH in the range of about 5 to 9. Suitable bases include alkali or alkaline earth metal carbonates, borates or phosphates, while suitable acids include benzoic, malic, pyruvic, ascorbic, sorbic, tartaric, fumaric, citric, maleic and adipic. Buffers may also be employed such as alkali metal phosphates, alkali metal borates, alkali metal carbonates and mixtures thereof.

This invention may be better understood with reference to the following examples.

EXAMPLE 1

Approximately 1.5 g of an activated carbon having a surface area of 1,000 m$^2$/g and a pore volume of 1.18 ml/g were placed in a container having 10 ml of an aqueous solution containing 3 wt. % H$_2$O$_2$, based on the weight of the solution, and having a pH of 5.8±0.5. The decomposition rates set forth below were observed using Merckoquant ® 10011 Peroxide Test strips, accurate to 1 ppm:

| Time, Hours | ppm residual H$_2$O$_2$ |
| --- | --- |
| 0.5 | ≦30.0 |
| 1.5 | ≦30.0 |
| 4.0 | 10.0 |
| 5.0 | 3.0 |
| 6.0 | 1.5 |

EXAMPLE 2

The purpose of this experiment was to determine the number of cycles which an activated carbon could be used and still decompose H$_2$O$_2$ below 40 ppm. Two grams of an activated carbon having a surface area of 850-900 m$^2$/g and a pore volume of 1.0 ml/g placed in a container having 10 ml of a 3 wt. % aqueous H$_2$O$_2$ solution having a pH of 5.8±0.5. After each measurement using Merckoquant ® 10 011 Peroxide Test strips, the activated carbon was reused with a fresh batch of 10 ml of a 3 wt. % aqueous H$_2$O$_2$ solution having a pH of 5.8±0.5.

| No. of Cycles | Residual H$_2$O$_2$ At | |
|---|---|---|
| | 3 Hours | 6 Hours |
| 1 | 30 ppm | 10 ppm |
| 22 | — | 30 ppm |

These results show that the activated carbon loses its activity very slowly. Since the activated carbon has such a large surface area with many active functional sites, it may be used either as a single-use dose or as a multiple-use dose.

EXAMPLE 3

Example 3 was carried out in the same manner as Example 2, except the amount of activated carbon was increased from 2 grams to 4 grams in order to insure that the level of residual H$_2$O$_2$ remaining at the end of 6 hours of contact with the activated carbon would be in the safe and acceptable range of 3-10 ppm.

| No. of Cycles | Residual H$_2$O$_2$ at 6 hrs. |
|---|---|
| 1 | 3 ppm |
| 25 | 3 ppm |
| 40 | 3 ppm |
| 50 | 3-10 ppm |

EXAMPLE 4

In this experiment, 2 g of an activated carbon having a surface area of 900 m$^2$/g and a pore volume of 0.8 ml/g were used to decompose 10 ml of a 3 wt. % aqueous H$_2$O$_2$ solution. The following decomposition rates were observed using Merckoquant ® 10 011 Peroxide Test strips:

| Time, hours | Residual H$_2$O$_2$ |
|---|---|
| 1 | 10 ppm |
| 2 | 0 ppm |

EXAMPLES 5-16

In the following examples, an aqueous solution containing 0.0315 wt. % NaOCl, based on the weight of the solution, was employed. Ten ml of this solution were added to ten ml of a pH 7 or PH 9 buffer solution.

To the combined NaOCl-buffer solutions were added about 3 g of the indicated activated carbon and the solutions were titrated with 0.005M Na$_2$S$_2$O$_3$ solution at the end of 1 hour and 4 hours contact times. The results are indicated in the tables set forth below:

| | Activated Carbon | | | |
|---|---|---|---|---|
| Ex. | wt. g | surf. area m$_2$/g | pore vol. ml/g | NaOCl, ppm, 1 hr. | NaOCl, ppm, 1 hr. |
| | | | pH 9 | | |
| 5 | 3.09 | Ex. 2 | Ex. 2 | 30.9 | 0.0 |
| 6 | 3.04 | Ex. 1 | Ex. 1 | 57.4 | 4.4 |
| 7 | 3.12 | 900 | 1.18 | 79.5 | 8.8 |
| 8 | 3.05 | 1050 | 0.95 | 4.4 | 0.0 |
| 9 | 3.02 | 700 | 0.85 | 48.2 | 8.8 |

-continued

| | Activated Carbon | | | |
|---|---|---|---|---|
| Ex. | wt. g | surf. area m$_2$/g | pore vol. ml/g | NaOCl, ppm, 1 hr. | NaOCl, ppm, 1 hr. |
| 10 | 3.04 | 650 | 0.85 | 110 | 30.9 |
| | | | pH 7 | | |
| 11 | 3.04 | Ex. 2 | Ex. 2 | 35.4 | 4.4 |
| 12 | 3.10 | Ex. 1 | Ex. 1 | 30.9 | 8.8 |
| 13 | 3.07 | 900 | 1.18 | 8.8 | 0.0 |
| 14 | 3.12 | 1050 | 0.95 | 30.9 | 0.0 |
| 15 | 3.01 | 700 | 0.85 | 30.9 | 1.2 |
| 16 | 3.05 | 650 | 0.85 | 30.9 | 8.8 |

What is claimed is:

1. A process for sterilizing a contact lens with an aqueous solution containing a sterilant comprising the steps of:
    (a) contacting a contact lens with an aqueous solution containing a sterilant selected from the group consisting of peroxygen disinfectants, inorganic hypochlorite compounds and hypochlorite precursor compounds, the amount of sterilant present in the solution and the time of contact of the lens with the solution being sufficient to effect sterilization of the lens; and thereafter
    (b) contacting the aqueous solution and lens resulting from step (a) with an amount of activated carbon and for a period of time sufficient to decompose substantially all of any residual sterilant to ophthalmologically innocuous by-products, said activated carbon having a surface area in excess of about 500 m$^2$/g and a pore volume of at least about 0.75 ml/g.

2. The process of claim 1 wherein the peroxygen disinfectant comprises hydrogen peroxide present in a concentration in the range of about 1 to 5 wt. %, based on the weight of the aqueous solution.

3. The process of claim 1, wherein the inorganic hypochlorite compound comprises sodium hypochlorite present in a concentration in the range of about 0.0005 to 0.5 wt. %, based on the weight of the aqueous solution.

4. The process of claim 1 wherein the aqueous solution is permitted to remain in contact with the lens for about 5 to 30 minutes before commencing step (b).

5. The process of claim 1 wherein the amount of aqueous solution employed in step (a) is about 5 to 25 ml and the amount of activated carbon employed in step (b) is about 1 to 5 grams.

6. The process of claim 1 wherein the activated carbon is permitted to remain in contact with the aqueous solution and lens resulting from step (a) for about 1 to 6 hours.

7. The process of claim 1 wherein the aqueous solution employed in step (a) has a pH in the range of about 5 to 9.

8. The process of claim 1 wherein the activated carbon employed in step (b) is present in a sealed container having a membrane which is permeable to the aqueous solution but is impermeable to the activated carbon.

9. The process of claim 1 wherein the activated carbon employed in step (b) is encapsulated in a water-swellable polymer which is permeable to the aqueous solution.

10. The process of claim 1 wherein the aqueous solution contains a buffer selected from the group consisting of alkali metal phosphates, alkali metal borates, alkali metal carbonates and mixtures thereof.

* * * * *